United States Patent [19]

Bundy

[11] 4,220,797

[45] Sep. 2, 1980

[54] NOVEL 9-DEOXY-16,16-DIMETHYL-PGF$_2$ COMPOUNDS, INTERMEDIATES AND PROCESS

[75] Inventor: Gordon L. Bundy, Portage, Mich.

[73] Assignee: The Upjohn Company, Kalamazoo, Mich.

[21] Appl. No.: 40,003

[22] Filed: May 18, 1979

[51] Int. Cl.$^2$ ............................................. C07C 177/00
[52] U.S. Cl. ................................ 560/121; 260/501.15; 260/501.18; 542/426; 562/503; 424/305; 424/316; 424/317
[58] Field of Search ......................... 560/121; 562/503; 260/501.15, 501.18

[56] References Cited

U.S. PATENT DOCUMENTS 4,033,989  7/1977  Bundy ................................... 560/121

*Primary Examiner*—Robert Gerstl
*Attorney, Agent, or Firm*—Robert A. Armitage

[57] ABSTRACT

The present invention provides novel 9α-methyl- or 9β-methyl-9-deoxy-16,16-dimethyl-PGF$_2$ compounds, and novel processes and intermediates for their preparation. Further provided are novel intermediates for the preparation of known 9-deoxy-9-methylene-16,16-dimethyl-PGF$_2$ compounds. The novel 9α- or 9β-methyl-9-deoxy-16,16-dimethyl-PGF$_2$ compounds are usefully employed as highly selective gastro-intestinal smooth muscle stimulators, rendering these novel compounds useful in the treatment of paralytic intestinal and bladder diseases. The novel compounds also possess the further advantage of exhibiting these gastro-intestinal smooth muscle effects, with reduced uterotonic and intestinal enteropooling effects as compared to the known 9-deoxy-PGF compounds.

9 Claims, No Drawings

4,220,797

NOVEL 9-DEOXY-16,16-DIMETHYL-PGF$_2$ COMPOUNDS, INTERMEDIATES AND PROCESS

TECHNICAL FIELD

The present invention provides novel prostaglandin analogs. Specifically, the present invention provides novel homologs of 9-deoxy-16,16-dimethyl-PGF$_2$, its salts and its esters. These novel homologs of 9-deoxy-16,16-dimethyl-PGF$_2$ compounds are 9α-methyl- or 9β-methyl-9-deoxy-16,16-dimethyl-PGF$_2$ compounds, i.e., 9-deoxy-16,16-dimethyl-PGF$_2$ compounds substituted at the C-9 position by a methyl group in either the alpha (below the plane of the cyclopentane ring) or beta (above the plane of the cyclopentane ring) configuration.

The present invention further relates to novel processes for preparing these homologous 9-deoxy-16,16-dimethyl-PGF$_2$ compounds. Further provided are novel chemical intermediates employed in these novel processes.

Finally provided by the present invention are novel processes and intermediates for preparing 9-deoxy-9-methylene-16,16-dimethyl-PGF$_2$ compounds. Such intermediates and processes for preparing these 9-deoxy-9methylene-16,16-dimethyl-PGF$_2$ compounds employ in part the novel intermediates referred to above for the preparation of the homologous 9-deoxy-16,16-dimethyl-PGF$_2$ compounds of the present invention.

The naturally occurring prostaglandins include compounds such as PGF$_{2\alpha}$, depicted by formula I. Formula I further indicates the carbon atom numbering for the natural prostaglandins. With respect to formula I, the art recognized system for the depiction of stereochemistry is employed, such that the dotted lines depicting substituents at C-8, C-9, C-11, and C-15 are of the alpha configuration or below the plane of the cyclopentane ring, while the C-12 substituent, depicted by a heavy solid line, is above the plane of the cyclopentane ring. When wavy lines are employed in formulas herein, reference is made thereby to substituents either in the alpha configuration or the beta configuration or a mixture of alpha and beta configurations. The manner of depiction of the various formulas herein is the same as that described in U.S. Pat. No. 4,060,534. Moreover, various terms of art, such as the definition of the term "prostaglandins analogs" as well as other conventions with respect to nomenclature and the like are the same as that described in U.S. Pat. No. 4,060,534, the relevant portions of which are incorporated by reference. Prior Art Numerous 9-deoxy-PGF-type compounds are known in the art. Most pertinent among such compounds are the 9-deoxy-16,16-dimethyl-PGF$_2$ compounds of U.S. Pat. No. 4,156,087, issued May 22, 1979.

Further known in the art are 9-deoxy-9-methylene-PGF-type compounds and methods for their preparation. Specifically, 9-deoxy-9-methylene-16,16-dimethyl-PGF$_2$ is described in U.S. Pat. No. 4,060,534, issued November 29 1977 and U.S. Pat. No. 4,130,720, issued Dec. 19 1978.

Also known in the art are the 9-deoxy-PG's of U.S. Pat. Nos. 3,808,259, 3,894,009, 3,678,092, 3,842,116, and 3,845,096.

SUMMARY OF THE INVENTION

The present invention particularly provides:

(a) A prostaglandin intermediate of formula III, IV, V, or VI
wherein R$_{10}$ is a stable, acid-hydrolyzable, blocking group; and
wherein —SiR$_{25}$R$_{26}$R$_{27}$ is a stable trialkylsilyl protective group wherein R$_{25}$, R$_{26}$ and R$_{27}$ are all alkyl of one to 6 carbon atoms, inclusive, with the proviso that at least one of R$_{25}$, R$_{26}$, and R$_{27}$ is tertiary alkyl; and (b) a prostaglandin analog of formula II
wherein R$_1$ is hydrogen, alkyl of one to 12 carbon atoms, inclusive, cycloalkyl of 2 to 10 carbon atoms, inclusive, aralkyl of 7 to 12 carbon atoms, inclusive, phenyl, phenyl substituted with one, 2, or 3 chloro or alkyl of one to 3 carbon atoms, inclusive, or a pharmacologically acceptable cation.

The stable, acid-hydrolyzable blocking groups within the scope of R$_{10}$ are groups which replace the hydroxy hydrogen, but are neither attacked by nor are reactive to the reagents in the transformations herein as the free hydroxyl group and which are subsequently replaceable with hydrogen in the preparation of the prostaglandin-type products. Several such blocking groups are known in the art, e.g., tetrahydropyranyl and substituted tetrahydropyranyl. See, for reference, E. J. Corey, Proceedings of the Robert A. Welch Foundation Conferences on Chemical Research, 12, Organic Synthesis, pages 51–79 (1969). Blocking groups according to R$_{10}$ which are useful for the instant purposes includes (a) tetrahydropyranyl;
(b) tetrahydrofuranyl; and
(c) —C(OR$_{21}$) (R$_{22}$)—CH(R$_{23}$)(R$_{24}$)
wherein R$_{21}$ is alkyl of one to 18 carbon atoms, inclusive, cycloalkyl of 3 to 10 carbon atoms, inclusive, aralkyl of 10 to 12 carbon atoms, inclusive, phenyl, or phenyl substituted with one, 2, or 3 alkyl of one to 4 carbon atoms, inclusive,
wherein R$_{22}$ and R$_{23}$ are alkyl of one to 4 carbon atoms, inclusive, phenyl, phenyl substituted with one, 2, or 3 alkyl of one to 4 carbon atoms, inclusive, or when R$_{22}$ and R$_{23}$ are taken together —(CH$_2$)a— or —(CH$_2$)$_b$—O—(CH$_2$)$_c$, wherein a is 3, 4, or 5, b is 1, 2, or 3, and c is 1, 2, or 3, with the proviso that the sum of b and c is 2, 3, or 4, with the further proviso that R$_{22}$ and R$_{23}$ may be the same or different, and
wherein R$_{24}$ is hydrogen or phenyl.

Of the silyl groups of the formula —OSiR$_{25}$R$_{26}$R$_{27}$, preferably one of R$_{25}$, R$_{26}$ and R$_{27}$ is tertiary-butyl and t-butyldimethylsilyl is the preferred group of the formula —OSiR$_{25}$R$_{26}$R$_{27}$.

When the stable, acid hydrolyzable blocking group R$_{10}$ is tetrahydropyranyl, the tetrahydropyranyl ether derivative of the hydroxy of the PG-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula —C(OR$_{21}$)(R$_{22}$)—CH(R$_{23}$)(R$_{24}$), wherein $R_{21}$, $R_{22}$, $R_{23}$, and $R_{24}$ are as defined above, the approporiate reagent is a vinyl ether, e.g., isobutyl vinyl ether or any vinyl ether of the formula $C(OR_{21})(R_{22})=C(R_{23})(R_{24})$, or an unsaturated cyclic or heterocyclic compound, e.g., 1-cyclohexen-1-yl methyl ether, or 4,5-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temberatures below 55° C., hydrolysis of the blocking groups is achieved.

For the silyl group referred to above, methods of preparation are known in the art. See Pierce, "Silylation of Organic Compounds" Pierce Chemical Company, Rockford, Ill. (1968). These silyl groups are selectively removed in the presence of the blocking groups according to $R_{10}$ by the use of tetra-n-butyl ammonium fluoride in tetrahydrofuran by the method of Corey, E. J., et al., JACS 94:6190 (1972).

The novel prostaglandin analogs of the present invention, the compounds according to formula II, are all 9α-methyl- or 9β-methyl-9-deoxy-16,16-dimethyl-PGF$_2$ acids, esters, or salts, depending upon the configuration of the methyl group at C-9.

These novel prostaglandin analogs are all highly useful stimulators of gastro-intestinal and bladder smooth muscle tissues, rendering these compounds highly useful in the treatment of paralytic diseases of the gastro-intestinal tract, particularly paralytic intestinal diseases, and paralytic bladder diseases, e.g., bladder atonia. In this respect, the novel compounds of the present invention are employecd for these purposes by the same methods, at the same dosages, and in the same pharmaceutical compositions as are known in the art for the prior art 9-deoxy-PGF$_2$ compounds of U.S. Pat. No. 4,033,989, issued July 7 1977, the relevant disclosure of which is incorporated here by reference. In contrast, however, to the prior art 9-deoxy-16,16-dimethyl-PGF$_2$ compounds of U.S. Pat. Nos. 4,033,989 and 4,156,087, the novel 9α- or 9β-methyl:9-deoxy-16,16-dimethyl-PGF$_2$ compounds exhibit the same order of potency as gastro-intestinal or bladder smooth muscle stimulatory agents, but exhibit uterotonic smooth muscle stimulator potencies and diarrheogenic enteropooling potencies one or two orders of magnitude less than that known in the prior art 9-deoxy-16,16-dimethyl-PGF$_2$ compounds. Hence, these novel 9α- or 9β-methyl-9-deoxy-16,16-dimethyl-PGF$_2$ compounds represent surprising and unexpectedly improved agents for the treatment of paralytic gastro-intestinal or bladder diseases. In this regard, 9α-methyl-9-deoxy-16,16-dimethyl-PGF$_2$ is an especially selective gastrointestinal smooth muscle stimulator as measured by standard animal tests, being roughly twice as potent as the known 9-deoxy-16,16-dimethyl-PGF$_2$. However, 9α-methyl-9-deoxy-16,16-dimethyl-PGF$_2$ retains only about 2% of the enteropooling and 5% of the uterine smooth muscle stimulatory potency of the prior art 9-deoxy-16,16-dimethyl-PGF$_2$ in standard laboratory tests. Thus, employing the novel compounds of the instant invention for treating these paralytic gastro-intestinal or bladder diseases results in a diminution of the profuse watery diarrhea resulting from enteropooling and reduced uterotonic activity.

As indicated above, the surprising and unexpected advantages of the instant compounds in the treatment of paralytic gastro-intestinal and bladder diseases are readily assessed by standard laboratory systems for evaluating prostaglandins and related compounds. These systems include the uterine smooth muscle activity in the monkey by an intravenous route of administration, the induction of enteropooling in the rat by oral dosing, and the potency in stimulating the gerbil colon in vitro. The relative potencies of 9-deoxy-16,16-dimethyl-PGF$_2$ and its novel 9α-methyl- and 9β-methyl-homologs in these standard test systems is reported in Table A.

Accordingly, the novel compounds of the instant invention are employed in man and valuable domestic animals in the treatment of numerous conditions and diseases, e.g., paralytic ileus, post-operative ileus, and post-operative bladder atonia, by methods and compositions known in the art. Most preferably, the novel compounds of the instant invention are administered orally in the form of conventional oral dosage forms for prostaglandins or rectally by suppositories. In the treatment, however, of paralytic bladder diseases, the novel prostaglandin analogs of the instant invention may be introduced directly into the bladder, either by injection or secondarily to catheterization. By any route of administration, however, the surprising and unexpected advantages of the instant compounds over the prior art 9-deoxy-16,16-dimethyl-PGF$_2$ compounds are obtained.

The novel prostaglandin analogs are employed for the purposes described above in free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

Charts A-D herein describe the preparation of intermediates for preparing the novel 9-deoxy-16,16-dimethyl-$PGF_2$ homologs and prior art 9-deoxy-16,16-dimethyl-$PGF_2$ compounds (Chart A), the novel process and intermediates for preparing the prior art 9-deoxy-9-methylene-16,16-dimethyl-$PGF_2$ compounds (Chart B), and the respective processes and intermediates for preparing the novel $9\alpha$- or $9\beta$-methyl compounds (Charts C and D, respectively).

With respect to the charts, $R_{10}$, $R_{25}$, $R_{26}$, and $R_{27}$ are as defined above and Ms is methylsulfonyl.

With respect to these charts, the prostaglandin analogs are prepared therein in free acid form. These free acids are, however, readily transformed to corresponding pharmacologically acceptable cations and esters according to $R_1$ by methods known in the art. A review of such salification and esterification methods is provided in U.S. Pat. No. 4,060,534.

The procedure of Chart A wherein $R_{10}$ is tetrahydropyranyl and —$SiR_{25}R_{26}R_{27}$ is t-butyldimethylsilyl is described in Example 1. When other silyl and blocking groups are substituted, procedures described above are employed. Similarly, the preparation of 9-deoxy-9-methylene-16,16-dimethyl-$PGF_2$ (Formula XXXV) of Chart B is described in Example 2. Further, the preparation of $9\alpha$-methyl-9-deoxy-16,16-dimethyl-$PGF_2$ (Formula XLV) of Chart C is described by Example 3.

Finally, the preparation of $9\beta$-methyl-9-deoxy-16,16-dimethyl-$PGF_2$ (Formula LV) of Chart D is described by Example 4.

Each of the Charts A-D describes a novel process in accordance with the present invention, as well as the novel intermediates claimed above.

DESCRIPTION OF THE PREFERRED EMBODIMENTS

The following Examples more particularly describe the novel compounds and processes provided in accordance with the present invention.

Example 1

2-Decarboxy-2-(t-butyldimethylsilyl)oxymethyl-2,3,4,5,6-pentanor-9-deoxy-9-methylene-16,16-dimethyl-$PGF_1$, 11,15-bis(tetrahydropyranyl)ether (Formula XXV: $R_{10}$ is 2-tetrahydropyranyl and one of $R_{25}$, $R_{26}$, and $R_{27}$ is t-butyl and the others are methyl).

Refer to Chart A

A. $3\alpha,5\alpha$-Dihydroxy-$2\beta$-($3\alpha$-hydroxy-4,4-dimethyl-trans-1-octenyl)-$1\alpha$-cyclopentaneacetic acid, $\gamma$ lactone, 11,15-bis(tetrahydropyranyl)ether, 30.2 g, in 1500 ml of diethyl ether is treated with 2.6 g of lithium aluminum hydride, added in small portions. The resulting suspension is then stirred for 90 min at 25° C., cooled to 0° C., and treated with 5.26 ml of water. Thereafter treatment of the resulting mixture of 4.2 ml of 10% aqueous sodium hydroxide yields a suspension which is stirred for 18 hr at 25° C. Following addition of magnesium sulfate, the reaction mixture is then filtered through diatomaceous earth (medium porosity) and the solids washed with diethyl ether. Concentration of the filtrate under reduced pressure yields a residue, 29.5 g, of a colorless viscous oil, the formula XXII compound: 2-Decarboxy-2-hydroxymethyl-2,3,4,5,6-pentanor-16,16-dimethyl-$PGF_{1\alpha}$ 11,15-bis(tetrahydropyranyl)ether. Silica gel TLC $R_f$ is 0.35 in ethyl acetate and hexane (7:3).

B. To a stirred solution at −30° C. of the reaction product of Part A (31.6 g) and 250 ml of dimethylformamide is added 9.23 g of imidazole, followed by addition of 10.37 g of t-butyldimethylsilyl chloride. The resulting mixture is then stirred for 2 hr at −30° to −40° C., allowed to warm to 20° C. for 48 hr, diluted with 400 ml of water, and isolated by extraction with diethyl ether. The ethereal extracts are then washed with aqueous potassium bisulfate, aqueous sodium bicarbonate and brine, dried over sodium sulfate, and concentrated under reduced pressure to a residue (37.6 g) of formula XXIII compound: 2-Decarboxy-2-(t-butyldimethylsilyl)oxymethyl-2,3,4,5,6-pentanor-16,16-dimethyl-$PGF_{1\alpha}$ 11,15-bis(tetrahydropyranyl)ether. Silica gel TLC $R_f$ is 0.68 in ethyl acetate and hexane (7:3). Infrared absorptions are observed at 3600, 1250, 1070, 1030, 1020, 1000, 975, 835, and 775 cm-1.

C. With the exclusion of moisture under nitrogen atmosphere, to a stirred solution of 47.4 ml of pyridine in 600 ml of methylene chloride is added 22.75 g of anhydrous chromium trioxide. This oxidation reagent is then stirred for 30 min at 25° C. and treated with diatomaceous earth. The reaction product of Part B (26.7 g) in 60 ml of methylene chloride is then added with stirring. The resulting mixture is then stirred for 45 min at 25° C., poured into a column containing silica gel (1 kg) and eluted with ethyl acetate. Fractions containing the formula XXIV product, 2-Decarboxy-2-(t-butyldimethylsilyl)oxymethyl-2,3,4,5,6-pentanor-16,16-dimethyl-$PGE_1$, 11,15-bis(tetrahydropyranyl) ether, are concentrated under reduced pressure to a residue, azeotroped with toluene. Chromatography on 3.5 kg of silica gel packed and eluted with ethyl acetate in hexane (1:4) yields 24.8 g of pure formula XXIV product as a pale yellow oil. Silica gel TLC $R_f$ is 0.35 to 0.38 (tetrahydropyranyl diastereomers) in ethyl acetate and hexane (1:4). Infrared absorptions are observed at 1740, 1460, 1380, 1250, 1200, 1050, 1040, 1010, 975, 835, 775 cm$^{-1}$. NMR absorptions in deuterochloroform are observed at 0.05, 0.92, 3.2–4.2, 4.6–5.0, and 5.5–5.9δ. The mass spectrum exhibits peaks at 421, 397, 394, 337, 319, 237, and 85.

D. A solution of 1.49 g of methylphenyl-N-methylsulfoximine in 10 ml of anhydrous tetrahydrofuran is cooled to 0° C. and treated under a nitrogen atmosphere with 2.95 ml of 3 methylmagnesium chloride in tetrahydrofuran. After 10 min at 0° C., a solution of 1.7 g of the reaction product of Part C and 2 ml of tetrahydrofuran is added and the resulting light yellow solution is stirred for 1 hr at 0° C. and 1 hr at 25° C. The reaction mixture is then treated with 30 ml of acetic acid and water (1:1), followed by addition of aluminum amalgam made from 2.7 g of 20 mesh aluminum. The reaction is then cooled in an ice bath to 15°–20° C. If the reaction is proceeding with excessive evolution of heat, up to two additional volumes of tetrahydrofuran is added to the reaction mixture prior to treatment with the aluminum amalgam. After 45 min, the reaction mixture is then filtered through diatomaceous earth (medium porosity) and the solids washed with ethyl acetate. The organic phase is then washed successively with brine, aqueous sodium bicarbonate and brine, dried over sodium sulfate, and concentrated to a residue. Chromatographing the residue on 200 g of silica gel packed and eluted with ethyl acetate and hexane (1:9) yields 1.22 g of pure 2-Decarboxy-2-(t-butyldimethylsilyl)oxymethyl-2,3,4,5,6pentanor-9-deoxy-9-methylene-16,16-dimethyl-PGF$_1$, 11,15-bis(tetrahydropyranyl)ether, a formula XXV compound. Silica gel TLC R$_f$ is 0.67 in ethyl acetate and hexane (1:4). Infrared absorptions are observed at 1580, 1460, 1440, 1260, 1200, 1100, 1070, 1020, 1000, 995, 815 and 770 cm$^{-1}$. NMR absorptions in deuterochloroform are observed at 5.65–5.3, 5.0–4.8, 4.8–4.55, 4.2–3.2, 0.85, and 0.04δ. The mass spectrum exhibits absorptions at 419, 395, 377, and 85.

EXAMPLE 2

9-Deoxy-9-methylene-16,16-dimethyl-PGF$_2$ (Formula XXXV).

Refer to Chart B

A. To a stirred solution of 1.2 g of the formula XXXI compound, the title product of Example 1, in 20 ml of tetrahydrofuran is added 12 ml of 0.75 M tetra-n-butylammonium fluoride in tetrahydrofuran. The resulting solution is then stirred under nitrogen for 1.5 hr, poured into brine and sodium bicarbonate, extracted with ethyl acetate, washed with brine, dried over anhydrous sodium sulfate, concentrated to a residue, and chromatographed on 100 g of silica gel (packed and eluted with ethyl acetate in hexane, 1:4). Pure 2-Decarboxy-2-hydroxymethyl-2,3,4,5,6-pentanor-9-deoxy-9-methylene-16,16-dimethyl-PGF$_1$, 11,15-bis(tetrahydropyranyl)ether, 880 mg, is obtained. Silica gel TLC R$_f$ is 0.2 in ethyl acetate and hexane (1:4). Infrared absorptions are observed at 3450, 1660, 1580, 1240, 1200, 1120, 1020, 975, and 875 cm$^{-1}$. NMR absorptions in deuterochloroform are observed at 5.7–5.35, 5.0–4.8, 4.8–4.4, and 4.2–3.2δ.

B. With exclusion of moisture under nitrogen atmosphere, 7.8 ml of pyridine and 100 ml of methylene chloride is treated with 5.11 g of chromium trioxide. After 15 min at 25° C., the oxidation reagent is cooled to 0° C., treated with diatomaceous earth, and treated with a solution of 3.9 g of the reaction product of Part A in 15 ml of methylene chloride. The resulting mixture is then stirred for 1.5 hr at 0° C. for 30 min at 25° C. The reaction mixture is then chromatographed on 500 g of silica gel eluted with ethyl acetate and the total eluant concentrated under reduced pressure to a residue. Chromatography on 400 g of silica gel packed and eluted with 20% ethyl acetate in hexane yields 3.54 g of formula XXXIII compound: 2-Decarboxy-2-formyl-2,3,4,5,6-pentanor-9-deoxy-9-methylene-16,16-dimethyl-PGF$_1$, 11,15-bis(tetrahydropyranyl)ether. Silica gel TLC R$_f$ is 0.50 in ethyl acetate and hexane (1:4). Infrared absorptions are observed at 1720, 1200, 1120, 1070, 1020, 975, and 870 cm$^{-1}$. The mass spectrum exhibits a high resolution peak at 363.2153 and other peaks at 279, 276, 195, 177, and 85.

C. With exclusion of moisture under nitrogen atmosphere a stirred suspension of 1.46 g of 50% sodium hydride in mineral oil and 35 ml of anhydrous dimethylsulfoxide is heated to 65° C. for 2 hr under a nitrogen atmosphere. This reaction mixture is then cooled to 25° C. and 6.8 g of 4-carboxybutyltriphenylphosphonium bromide is added. The resulting dark red solution is then stirred at 25° C. for 30 min, transferred to a stirred solution of 3.54 g of the reaction product to Part B and 5 ml of dimethylsulfoxide and stirred for 18 hr at 25° C. The resulting mixture is then poured into brine, acidified with aqueous potassium bisulfate, extracted, with ethyl acetate and hexane (1:1), washed with brine, dried over sodium sulfate and concentrated to a residue of the formula XXIV compound, 9-deoxy-9-methylene-16,16-dimethyl-PGF$_2$, 11,15-bis(tetrahydropyranyl)ether, 6 g. Silica gel TLC R$_f$ is 0.16.

D. The reaction product of Part C in 10 ml of tetrahydrofuran is diluted with 15 ml of acetic acid and 20 ml of water. The resulting solution is then stirred under nitrogen atmosphere at 45° C. for 5 hr, poured into brine, extracted with ethyl acetate, washed with brine, dried over anhydrous sodium sulfate, concentrated to a residue, and chromatographed on 400 g of acid-washed silica gel, packed and eluted with ethyl acetate and hexane (2:3). Formula XXXV title product, 9-deoxy-9-methylene-16,16-dimethyl-PGF$_2$, 1.94 g, is obtained.

EXAMPLE 3

9α-Methyl-9-deoxy-16,16-dimethyl-PGF$_2$ (Formula XLV)

Refer to Chart C

A. A solution of 2.0 g of the formula XLI compound, the title product of Example 1, in 100 ml of dry tetrahydrofuran is cooled to 0° C. under nitrogen atmosphere with stirring. A 3M excess of 9-BBN, 9-borabicyclo-[3.3.1]nonane, is added dropwise over 5 min. The reaction mixture is maintained at 0° C. for 4.5 hr, whereupon 9 ml of 30% aqueous hydrogen peroxide and 9 ml of 3 M aqueous potassium hydroxide is added. After warming to ambient temperature, the reaction mixture is washed with brine and the organic layer dried over sodium sulfate. Concentration under reduced pressure yields a crude oil which is chromatographed on 285 g of silica gel (high pressure liquid chromatography) packed and eluted with acetone and hexane (3:17). There is accordingly obtained 1.07 g of formula XLII compound, 2-decarboxy-2-(t-butyldimethylsilyl)oxymethyl-2,3,4,5,6-pentanor-9-deoxy-9α-hydroxymethyl-16,16-dimethyl-PGF$_1$, 11,15-bis(tetrahydropyranyl)ether. NMR absorptions in deuterochloroform are observed at 0.9, 1.2–2.9, 2.05, 3.5–4.0, 4.7, and 5.4–5.7δ. Infrared absorptions are observed at 3400, 1720, 1480, 1375, 1245, 1100, 1020, 830, and 775 cm$^{-1}$. Silica gel TLC R$_f$ is 0.42 in acetone and hexane (1:4).

B. The reaction product of Part A (4.7 g) in 100 ml of methylene chloride is treated with 1.5 ml of triethylamine, followed by treatment with 1.64 ml of methanesulfonyl chloride. The reaction mixture, having been maintained at 0° C. under a nitrogen atmosphere during the addition, is warmed to ambient temperature and after 1 hr poured into brine containing 20 ml of 2 M potassium bisulfate. Extraction with ethyl acetate and repeated washing of the organic extracts with brine, drying over sodium sulfate, and concentration under reduced pressure to a residue yields the formula LXIII compound: 2-Decarboxy-2-(t-butyldimethylsilyl)oxymethyl- 2,3,4,5,6-pentanor-9-deoxy-9α-methanesulfonyloxymethyl-16,16 dimethyl-PGF$_1$, 11,15-bis(tetrahydropyranyl)ether, 6.7 g. Silica gel TLC R$_f$ is 0.68 in ethyl acetate and hexane (2:3).

C. Under a nitrogen atmosphere 1.0 g of the reaction product of Part B is treated with 200 mg of lithium tetrahydro-aluminate in 15 ml of tetrahydrofuran (2 aliquot at 1 hr intervals). The resulting mixture is then allowed to stir at ambient temperature for 24 hr, whereupon 0.4 ml of water and 0.32 ml of 10% aqueous sodium hydroxide is added. The resulting mixture is then stirred for 24 hr, the aluminum salts filtered off with diatomaceous earth, and the solvent evaporated to yield a clear colorless oil. Chromatorgraphy on 100 g of silica gel packed and eluted with acetone and hexane (1:19) yields 606 mg of pure formula XLIV compound: 9α-methyl-9-deoxy-2-decarboxy-2-(t-butyldimethylsilyl)oxymethyl-2,3,4,5,6-pentanor-16,16-dimethyl-PGF$_1$, 11,15-bis(tetrahydropyranyl)ether. NMR absorptions in deuterochloroform are observed at 0.9, 0.92–2.9, 3.4–4.0, 4.7, and 5.4–5.6δ. Infrared absorptions are observed at 3000, 1480, 1375, 1245, 1190, 1100, 1020, 875, 770 cm$^{-1}$. Silica gel TLC R$_f$ is 0.75 in acetone and hexane (1:4).

D. Following the procedure of Example 2, there are obtained from 600 mg of the reaction product of Part C the following compounds:
  (a) 9α-methyl-9-deoxy-2-decarboxy-2-hydroxymethyl-2,3,4,5,6-pentanor-16,16-dimethyl-PGF$_1$, 11,15-bis(tetrahydropyranyl)ether, 470 mg. Infrared absorptions are observed at 3400, 3000, 1460, 1375, 1250, 1200, 1125, 1020, and 870 cm$^{-1}$. Silica gel TLC R$_f$ is 0.33 in acetone and hexane (1:4);
  (b) 9α-methyl-9-deoxy-2-decarboxy-2-formyl-2,3,4,5,6-pentanor-16,16-dimethyl-PGF$_1$, 11,15-bis(tetrahydropyranyl)ether, 418 mg. Silica gel TLC R$_f$ is 0.70 in ethylacetate and hexane (3:7);
  (c) 9α-methyl-9-deoxy-16,16-dimethyl-PGF$_2$, 11,15-bis(tetrahydropyranyl)ether. Silica gel TLC R$_f$ is 0.27 in ethyl acetate and hexane (1:4);
  (d) 9α-methyl-9-deoxy-16,16-dimethyl-PGF$_2$ (title product), 300 mg. NMR absorptions in deuterochloroform are observed at 0.8–1.0, 1.2, 1.3–2.5, 3.7–3.9, 5.3–5.7, and 6.3δ. Infrared absorptions are observed at 3400–2400, 1705, 1440, and 1225 cm$^{-1}$. Silica gel TLC R$_f$ is 0.28 in ethyl acetate and hexane (2:3) containing 1% acetic acid.

EXAMPLE 4

9β-Methyl-9-deoxy-16,16-dimethyl-PGF$_2$ (Formula LV)

Refer to Chart D

A. Under a nitrogen atmosphere with exclusion of moisture 650 mg of chromic acid, 25 ml of methylene chloride and 1 ml of pyridine are combined and stirred for 30 min at ambient temperature. Thereafter, diatomaceous earth is added and the resulting mixture combined with the product of Example 3, Part A (500 mg) in 5 ml of methylene chloride. After 10 min, the reaction mixture is filtered through silica gel, concentrated under reduced pressure to the formula LII compound: 2-Decarboxy-2-(t-butyldimethylsilyl)oxymethyl-2,3,4,5,6-pentanor-9-deoxy-9α-formyl-16,16-dimethyl-PGF$_1$, 11,15-bis(tetrahydropyranyl)ether. Infrared absorptions are observed at 1710, 1460, 1380, 1245, 1195, 1100, 1020, 975, 835, and 275 cm$^{-1}$. Silica gel TLC R$_f$ is 0.56 in ethyl acetate and hexane (1:4).

B. Under a nitrogen atmosphere 100 mg of the reaction product of Part A in 10 ml of methylene chloride is treated with 18.5 μl of DBU, 1,5-diazabicyclo[5.4.0]-undec-5-ene, and allowed to stir for 16 hr. Rinsing with 2 M potassium bisulfate and brine, drying over sodium sulfate, and concentrating under reduced pressure yields formula LIII compound: 2-Decarboxy-2-(t-butyldimethylsilyl)oxymethyl-2,3,4,5,6-pentanor-9-deoxy-9β-formyl-16,16-dimethyl-PGF$_1$, 11,15-bis(tetrahydropyranyl)ether. Silica gel TLC R$_f$ is 0.58 in ethyl acetate and hexane (1:4).

C. A solution of 1.8 g of the reaction product of Part B in 50 ml of methanol is maintained at 20° C. during addition of 500 mg of sodium borohydride. After vigorous stirring for 15 min, the reaction mixture is then poured into brine containing 10 ml of 2 M potassium bisulfate, extracted with ethyl acetate, washed with brine, dried over sodium sulfate, concentrated to a residue, and chromatographed on 300 g of silica gel packed and eluted with acetone and methylene chloride (1:19). Formula LIV product, 2-decarboxy-2-(t-butyldimethylsilyl)oxymethyl-2,3,4,5,6-pentanor-9-deoxy-9β-hydroxymethyl-16,16-dimethyl-PGF$_1$, 11,15-bis(tetrahydropyranyl)ether, 1.4 g, is obtained. Silica gel TLC R$_f$ is 0.31 in ethyl acetate and hexane (3:7).

D. Following the procedure of Example 3, Parts B-D, there are respectively obtained from 1.4 g of the reaction product of Part C above, the following compounds:
  (a) 2-Decarboxy-2-(t-butyldimethylsilyl)oxymethyl-2,3,4,5,6-pentanor-9-deoxy-9β-methanesulfonyloxymethyl-16,16-dimethyl-PGF$_1$, 11,15-bis(tetrahydropyranyl)ether. Silica gel TLC R$_f$ is 0.54 in ethyl acetate and hexane (3:7).
  (b) 9β-Methyl-9-deoxy-2-decarboxy-2-(t-butyldimethylsilyl)oxymethyl-2,3,4,5,6-pentanor-16,16-dimethyl-PGF$_1$, 11,15-bis(tetrahydropyranyl)ether, 564 mg. Silica gel TLC R$_f$ is 0.73 in ethyl acetate and hexane (3:7).
  (c) 9β-Methyl-9-deoxy-2-decarboxy-2-hydroxymethyl-2,3,4,5,6-pentanor-16,16-dimethyl-PGF$_{1α}$, 11,15-bis(tetrahydropyranyl)ether. Silica gel TLC R$_f$ is 0.40 in ethyl acetate and hexane (3:7).
  (d) 9β-Methyl-9-deoxy-2-decarboxy-2-formyl-2,3,4,5,6-pentanor-16,16-dimethyl-PGF$_1$, 11,15-bis(tetrahydropyranyl)ether. Silica gel TLC R$_f$ is 0.60 in ethyl acetate and hexane (3:7).
  (e) 9β-Methyl-9-deoxy-16,16-dimethyl-PGF$_2$, 11,15-bis(tetrahydropyranyl)ether.
  (f) 9β-Methyl-9-deoxy-16,16-dimethyl-PGF$_2$ (title product), 54% yield from 9β-methyl-9-deoxy-2-decarboxy-2-(t-butyldimethyldilyl)oxymethyl-2,3,4,5,6-pentanor-16,16-dimethyl-PGF$_1$, 11,15-bis(tetrahydropyranyl)ether. NMR absorptions in deuterochloroform are observed at 0.9–2.6, 3.9, 5.3–5.6, and 6.1δ. Infrared absorptions are observed at 3600–2200, 1705, 1560, 1480, 1400, 1220, and 975 cm$^{-1}$. Silica gel TLC R$_f$ is 0.28 in ethyl acetate and hexane (2:3) with 1% acetic acid.

The free acid products of Examples 3 and 4 are transformed into the corresponding salts and esters by conventional means.

TABLE A

Biological Activity of 9-Deoxy-16,16-Dimethyl-PGF$_2$ Compounds

| | Uterine SM Potency[a] | Enteropooling Potency[b] | GI-SM Potency[c] |
|---|---|---|---|
| 9-deoxy-16,16-dimethyl-PGF$_2$ | 1 | 1 | 1 |
| 9α-methyl-9-deoxy-16,16-dimethyl-PGF$_2$ | 0.05 | 0.02 | 1.8 |
| 9β-methyl-9-deoxy-16,16-dimethyl-PGF$_2$ | 0.1 | 0.1 | 0.7 |

[a]Potency (IV) in stimulation of primate (monkey) uterine smooth muscle.
[b]Potency (oral) in inducing enteropooling in the rat, associated with diarrhogenic potential.
[c]Potency (in vitro) in stimulating gerbil colon.

FORMULAS

CHART A

CHART B 4,220,797
-continued
CHART B
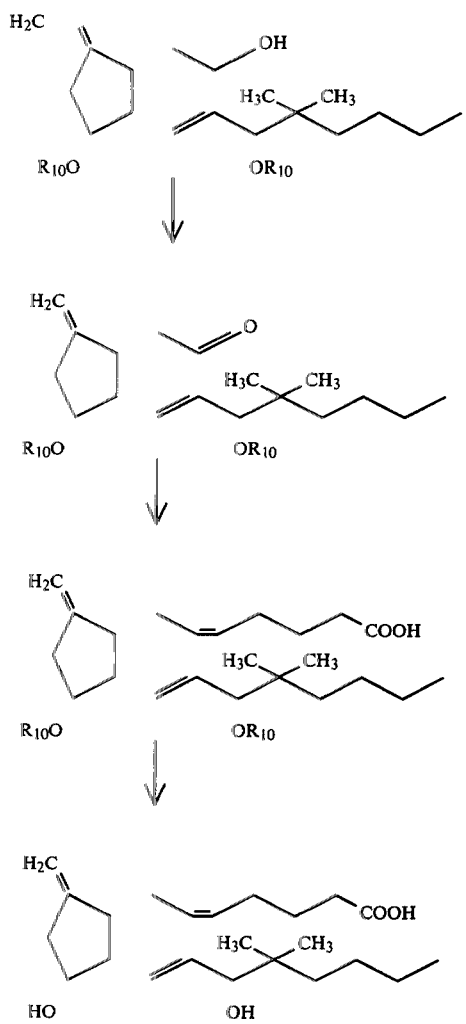
CHART C
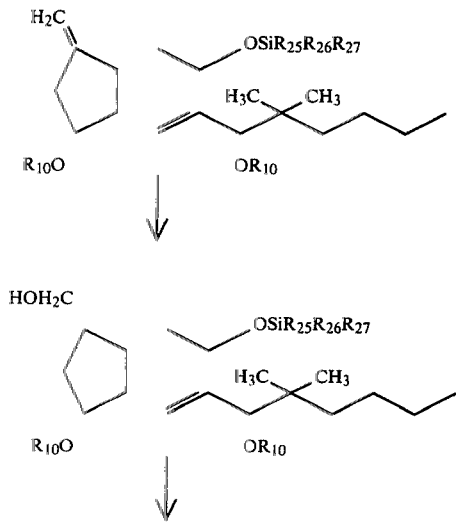
-continued
CHART C
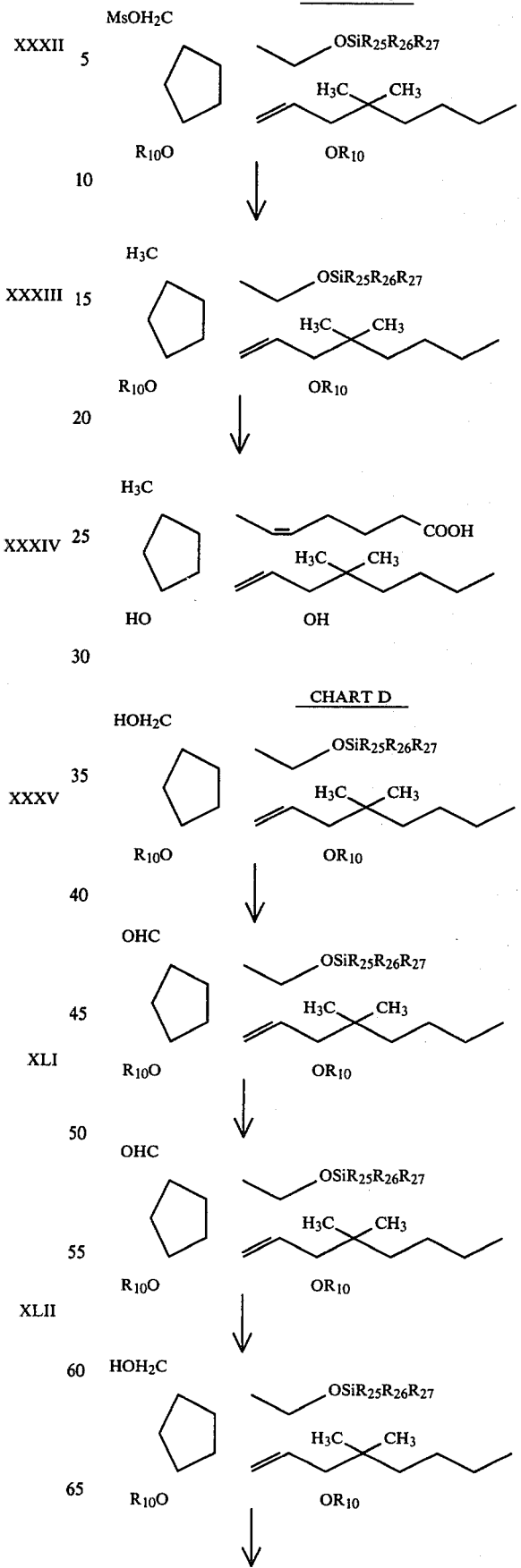

-continued
CHART D

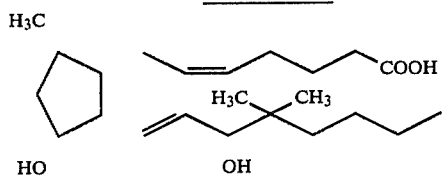

I claim:
1. A prostaglandin analog of formula II

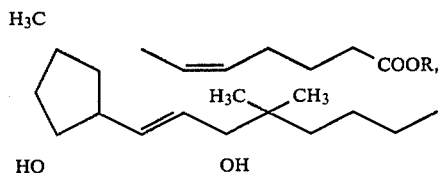 II wherein $R_1$ is hydrogen, alkyl of one to 12 carbon atoms, inclusive, cycloalkyl of 2 to 10 carbon atoms, inclusive, aralkyl of 7 to 12 carbon atoms, inclusive, phenyl, phenyl substituted with one, 2, or 3 chloro or alkyl of one to 3 carbon atoms, inclusive, or a pharmacologically acceptable cation.

2. 9α-Methyl-9-deoxy-16,16-dimethyl-PGF$_2$, methyl ester, a prostaglandin analog according to claim 1.

3. 9α-Methyl-9-deoxy-16,16-dimethyl-PGF$_2$, tris(hydroxymethyl)amino methane salt, a prostaglandin analog according to claim 1.

4. 9α-Methyl-9-deoxy-16,16-dimethyl-PGF$_2$, adamantanamine salt, a prostaglandin analog according to claim 2.

5. 9α-Methyl-9-deoxy-16,16-dimethyl-PGF$_2$, a prostaglandin analog according to claim 1.

6. 9β-Methyl-9-deoxy-16,16-dimethyl-PGF$_2$, methyl ester, a prostaglandin analog according to claim 1.

7. 9β-Methyl-9-deoxy-16,16-dimethyl-PGF$_2$, tris(hydroxymethyl)amino methane salt, a prostaglandin analog according to claim 1.

8. 9β-Methyl-9-deoxy-16,16-dimethyl-PGF$_2$, adamantanamine salt, a prostaglandin analog according to claim 1.

9. 9β-Methyl-9-deoxy-16,16-dimethyl-PGF$_2$, a prostaglandin analog according to claim 1.

* * * * *

UNITED STATES PATENT OFFICE
CERTIFICATE OF CORRECTION

Patent No. 4,220,797                    Dated 2 September 1980

Inventor(s) Gordon L. Bundy

It is certified that error appears in the above-identified patent and that said Letters Patent are hereby corrected as shown below:

Column 3, line 2, "apporopriate" should read -- appropriate --; line 39, "employecd" should read -- employed --; line 47, "9β-methyl:9-deoxy-" should read -- 9β-methyl-9-deoxy- --;
   Column 4, line 15, "is reported" should read -- are reported --;
   Column 6, line 62, "3 methylmagnesium" should read -- 3 N methyl-magnesium --;
   Column 9, line 14, "Chromatorgraphy" should read -- Chromatography --;
   Column 11, lines 22-68, should read as follows instead of as appears in the patent:

-- FORMULAS

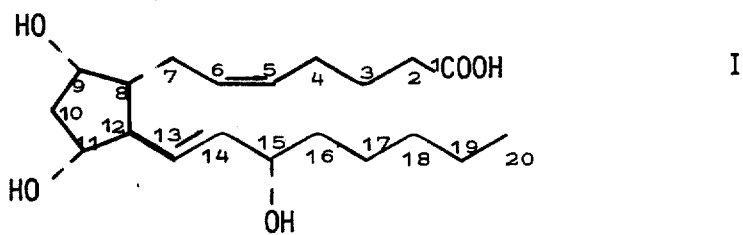

I

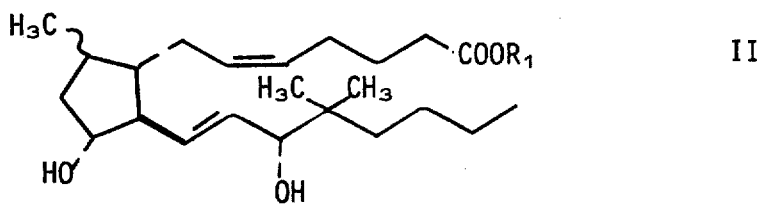

II

UNITED STATES PATENT OFFICE
CERTIFICATE OF CORRECTION

Patent No. 4,220,797     Dated 2 September 1980

Inventor(s) Gordon L. Bundy

It is certified that error appears in the above-identified patent and that said Letters Patent are hereby corrected as shown below:

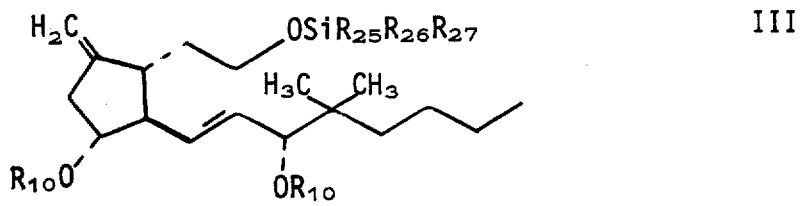   III

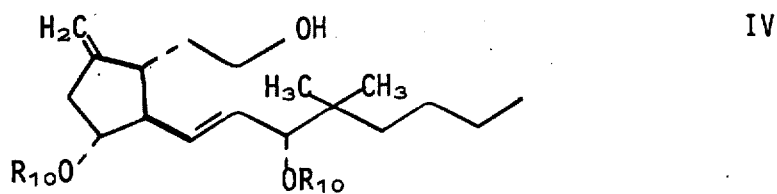   IV

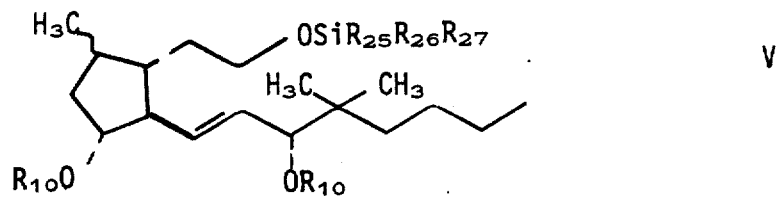   V

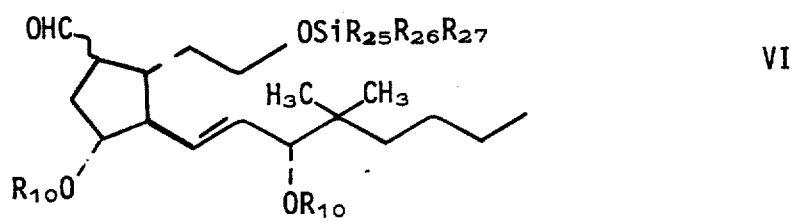   VI

--;

UNITED STATES PATENT OFFICE
CERTIFICATE OF CORRECTION

Patent No. 4,220,797          Dated 2 September 1980

Inventor(s) Gordon L. Bundy

It is certified that error appears in the above-identified patent and that said Letters Patent are hereby corrected as shown below:

Columns 12 through 14 should read as follows instead of as appears in the patent:

-- CHART A

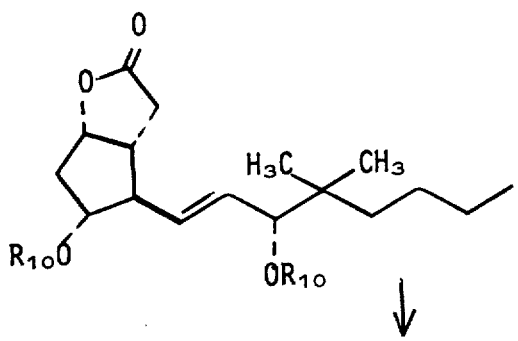

XXI

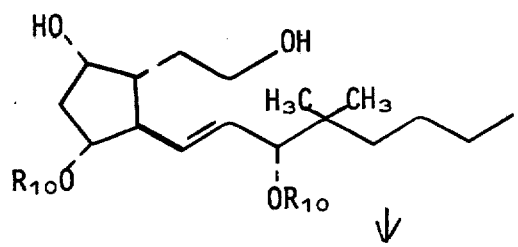

XXII

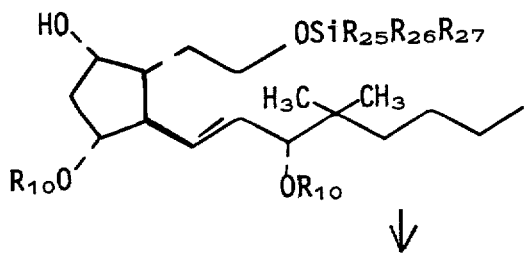

XXIII

UNITED STATES PATENT OFFICE
CERTIFICATE OF CORRECTION

Patent No. 4,220,797  Dated 2 September 1980

Inventor(s) Gordon L. Bundy

It is certified that error appears in the above-identified patent and that said Letters Patent are hereby corrected as shown below:

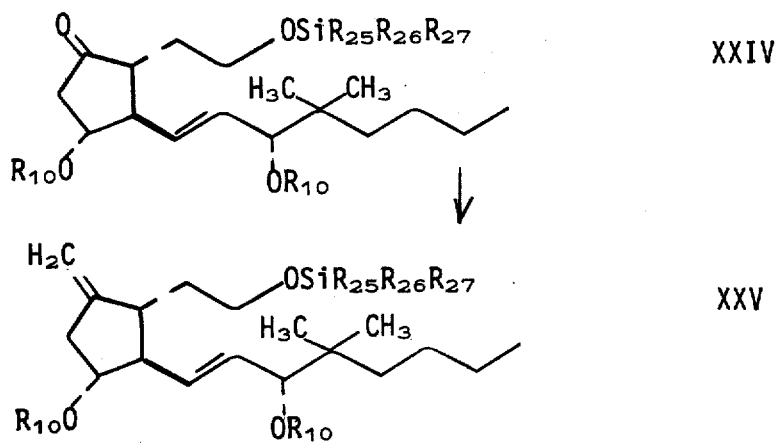

XXIV

XXV

CHART B

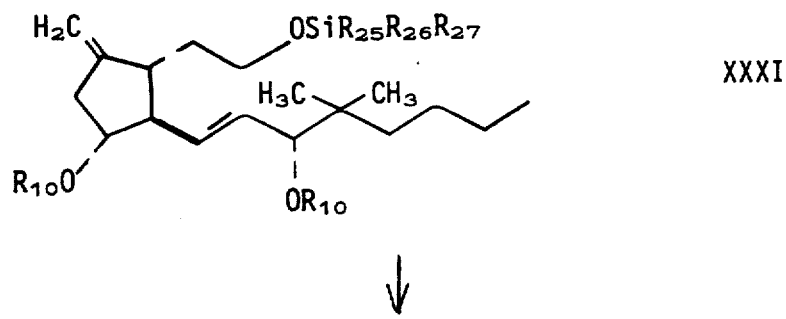

XXXI

UNITED STATES PATENT OFFICE
CERTIFICATE OF CORRECTION

Patent No. 4,220,797  Dated 2 September 1980

Inventor(s) Gordon L. Bundy

It is certified that error appears in the above-identified patent and that said Letters Patent are hereby corrected as shown below:

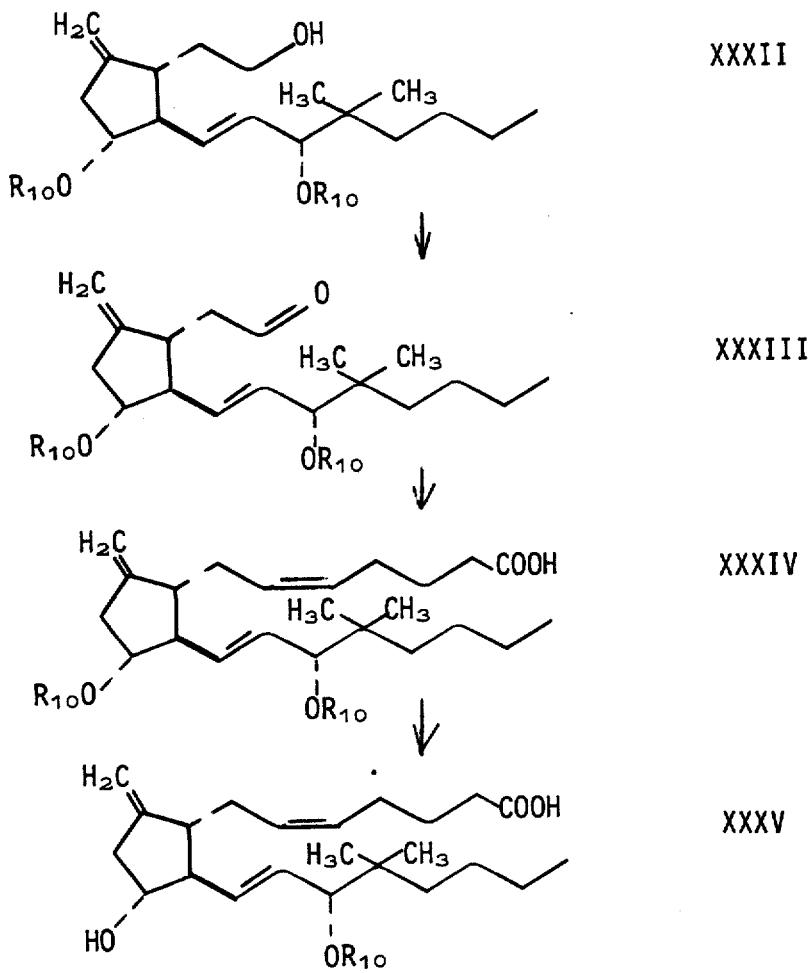

XXXII

XXXIII

XXXIV

XXXV

UNITED STATES PATENT OFFICE
CERTIFICATE OF CORRECTION

Patent No. 4,220,797  Dated 2 September 1980

Inventor(s) Gordon L. Bundy

It is certified that error appears in the above-identified patent and that said Letters Patent are hereby corrected as shown below:

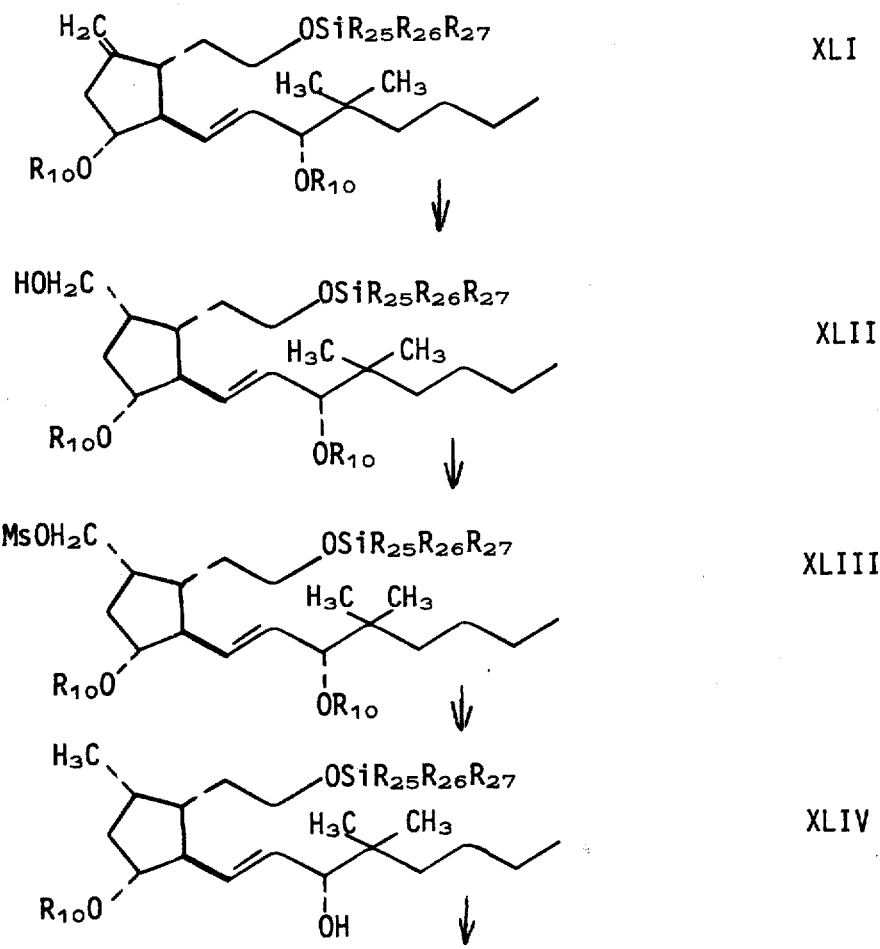

UNITED STATES PATENT OFFICE
CERTIFICATE OF CORRECTION

Patent No. 4,220,797　　　　Dated 2 September 1980

Inventor(s) Gordon L. Bundy

It is certified that error appears in the above-identified patent and that said Letters Patent are hereby corrected as shown below:

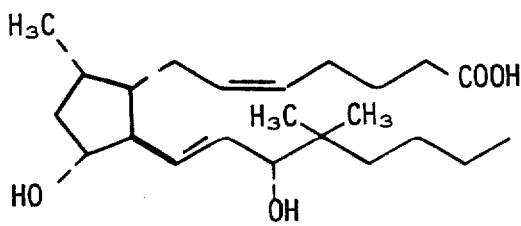 XLV

CHART D

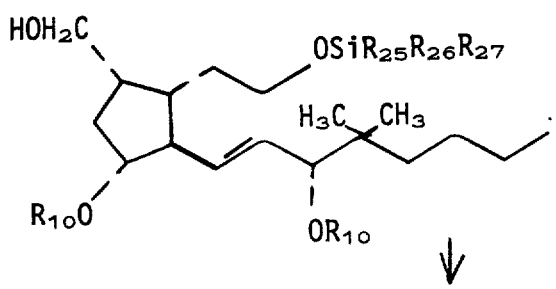 LI

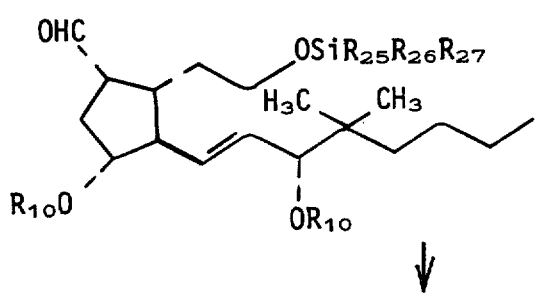 LII

UNITED STATES PATENT OFFICE
CERTIFICATE OF CORRECTION

Patent No. 4,220,797  Dated 2 September 1980

Inventor(s) Gordon L. Bundy

It is certified that error appears in the above-identified patent and that said Letters Patent are hereby corrected as shown below:

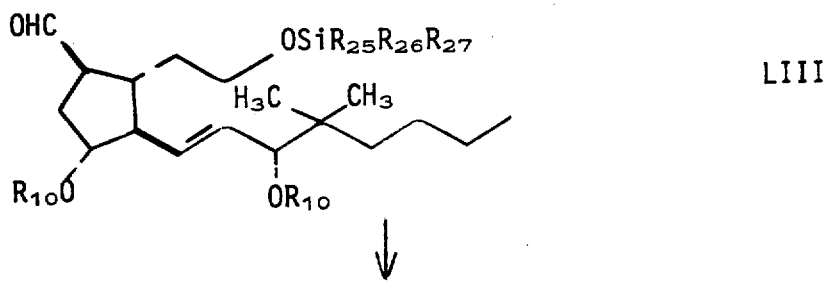

LIII

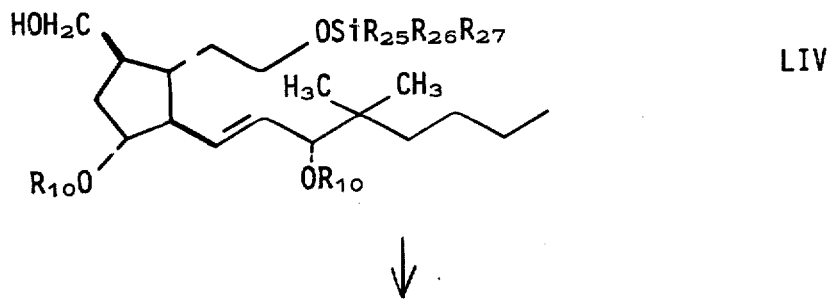

LIV

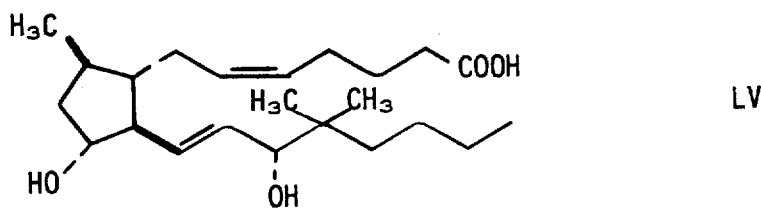

LV

UNITED STATES PATENT OFFICE
CERTIFICATE OF CORRECTION

Patent No. 4,220,797     Dated 2 September 1980

Inventor(s) Gordon L. Bundy

It is certified that error appears in the above-identified patent and that said Letters Patent are hereby corrected as shown below:

Column 15, lines 13-20, should read as follows instead of as appears in the patent:

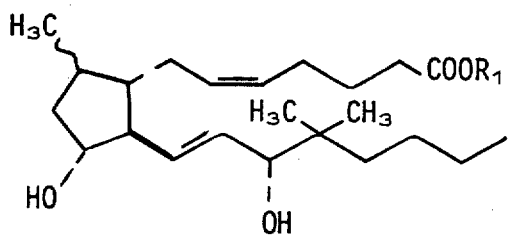

Signed and Sealed this

Twenty-first Day of April 1981

[SEAL]

Attest:

RENE D. TEGTMEYER

Attesting Officer    Acting Commissioner of Patents and Trademarks